United States Patent
Arai et al.

(10) Patent No.: US 9,233,235 B2
(45) Date of Patent: Jan. 12, 2016

(54) BALLOON CATHETER

(75) Inventors: Tsunenori Arai, Yokohama (JP);
 Natsumi Shimazaki, Yokohama (JP);
 Katsuya Miyagawa, Osaka (JP); Yuuki Nishimura, Osaka (JP); Misa Kakinoki, Osaka (JP)

(73) Assignees: KEIO UNIVERSITY, Tokyo (JP);
 NIPRO CORPORATION, Osaka (JP)

( * ) Notice: Subject to any disclaimer, the term of this patent is extended or adjusted under 35 U.S.C. 154(b) by 97 days.

(21) Appl. No.: 13/990,547

(22) PCT Filed: Dec. 12, 2011

(86) PCT No.: PCT/JP2011/006914
 § 371 (c)(1),
 (2), (4) Date: Jun. 12, 2013

(87) PCT Pub. No.: WO2012/081217
 PCT Pub. Date: Jun. 21, 2012

(65) Prior Publication Data
 US 2013/0267985 A1 Oct. 10, 2013

(30) Foreign Application Priority Data
 Dec. 13, 2010 (JP) .................................. 2010-277177

(51) Int. Cl.
 *A61B 18/28* (2006.01)
 *A61M 25/10* (2013.01)
 (Continued)

(52) U.S. Cl.
 CPC .............. *A61M 25/104* (2013.01); *A61B 18/04* (2013.01); *A61B 18/28* (2013.01); *A61B 2018/0022* (2013.01); *A61B 2018/00386* (2013.01); *A61B 2218/002* (2013.01)

(58) Field of Classification Search
 CPC ..... A61F 7/12; A61F 7/123; A61F 2007/126; A61B 18/02; A61B 18/04; A61B 18/08; A61B 18/28; A61B 2018/0022; A61B 2018/00386
 USPC ............................... 607/104–105; 606/28, 41
 See application file for complete search history.

(56) References Cited

U.S. PATENT DOCUMENTS

| 5,417,689 A | * | 5/1995 | Fine | 606/41 |
| 2005/0261626 A1 | * | 11/2005 | Arai et al. | 604/96.01 |
| 2009/0157066 A1 | * | 6/2009 | Satake | 606/27 |

FOREIGN PATENT DOCUMENTS

| JP | B2-2535250 | 9/1996 |
| JP | B2-2864094 | 3/1999 |

(Continued)

OTHER PUBLICATIONS

International Search Report issued in International Patent Application No. PCT/JP2011/006914 dated Jan. 10, 2012.
(Continued)

*Primary Examiner* — Jaymi Della
*Assistant Examiner* — Khadijeh Vahdat
(74) *Attorney, Agent, or Firm* — Oliff PLC

(57) ABSTRACT

A balloon catheter of novel configuration, which is capable of both efficiently heating a heating element by using a laser light and of ensuring durability by avoiding the laser light directly heating members other than the heating element. Provided is a balloon catheter with a balloon disposed in a distal end section of a shaft and wherein: a tightly wound coil shaped heating element is housed and arranged in the balloon; an optical fiber that irradiates a laser light inside the heating element is disposed; and a supply path that supplies a fluid to inside the balloon through an inside of the heating element and a discharge path that discharges the fluid from inside the balloon through a discharge port positioned on an outside of the heating element are disposed.

3 Claims, 2 Drawing Sheets

(51) Int. Cl.
*A61B 18/04* (2006.01)
*A61B 18/00* (2006.01)

(56) References Cited

FOREIGN PATENT DOCUMENTS

| JP | 2000-088022 A | 3/2000 |
|---|---|---|
| JP | A-2006-15064 | 1/2006 |

OTHER PUBLICATIONS

International Preliminary Report on Patentability issued in International Patent Application No. PCT/JP2011/006914 dated Jun. 18, 2013.
Jul. 7, 2015 Office Action issued in Japanese Patent Application No. 2012-548642.
Oct. 15, 2015 Office Action issued in Japanese Patent Application No. 2012-548642.

* cited by examiner

BALLOON CATHETER

TECHNICAL FIELD

The present invention relates to a balloon catheter for recovering blood flow by pushing open a stenosis portion by inserting a balloon into the stenosis portion of a blood vessel or the like and expanding it.

BACKGROUND ART

From the past, balloon catheters have been used with percutaneous transluminal coronary angioplasty (PTCA). A balloon catheter is equipped with a shaft through which a guide wire is inserted, and a balloon attached to the front end section of the shaft, and by supplying fluid into the balloon, the balloon is expanded at the stenosis portion of the blood vessel, and the stenosis portion is pushed open.

For the stenosis portion of the blood vessel that is pushed open by the balloon, with plain old balloon angioplasty (POBA), by pushing against the blood vessel wall a balloon for which the internal pressure of the balloon has been raised, the blood vessel wall is plastically deformed, and blood vessel expansion is realized.

However, with plain old balloon angioplasty, the problem of the blood vessel constricting again after treatment may occur. One reason for this is possibly due to the fact that the blood vessel wall is merely temporarily crushed by the pushing pressure of the balloon, and after the restriction by the balloon is released, it gradually recovers its original shape. As other reasons for restenosis, we can additionally list intimal thickening, negative remodeling or the like.

Also, when performing expansion of a stenosis portion using a balloon, similarly, blood vessel wall injury due to applying pressure is also a problem. Specifically, the stenosis portion is not necessarily flexible, and is typically harder than the other parts of the blood vessel, so sufficient pressurization of the balloon to push open the stenosis portion is required. However, when the pressure of the balloon is made high, there is the risk of injury occurring into the deep layer of the blood vessel, which is undesirable, and there was the risk of the blood vessel becoming stenosis again during treatment of the injury.

As one means of addressing these problems, for example in Japanese Published Patent No. JP-B-2535250 (Patent Document 1), a balloon catheter is proposed by which it is possible to realize deformability during expansion, and shape maintainability after expansion by adjusting the temperature of the blood vessel wall. Specifically, by heating the fluid inside the balloon and pushing the blood vessel wall open while warming it, it is possible to increase the flexibility of the blood vessel wall during expansion of the stenosis portion, so injury to the blood vessel due to expansion is prevented and restenosis is also avoided.

However, with the balloon catheter noted in Patent Document 1, a laser light absorbing heating tube heated by laser light is a braided structure made of stainless steel or the like, so it is easy for the flexibility to be insufficient, and it was difficult to ensure sufficient deformation following capability in relation to the blood vessel shape. In fact, fluid is made to be supplied inside the balloon through tiny gaps of the laser light absorbing heating tube with a braided structure, so it was necessary to spend a long time for balloon expansion deformation, and there was the problem that the surgery time became long, and this placed a big burden on the surgeon and the patient.

In addition, the front end fitting which adheres the front end section of the laser light absorbing heating tube is made of metal, and the front end fitting has a structure by which it is exposed to the outside (blood vessel interior), and the balloon and a third tube are also adhered to the front end fitting. Because of that, there is the risk that the front end fitting heated by laser light will contact the blood vessel wall and injure the blood vessel wall, and also the risk that the front end fitting will heat the balloon and third tube more than is necessary, bringing the risk of a decrease in durability or an injury.

Also, with Japanese Published Patent No. JP-B-2864094 (Patent Document 2), proposed is a constitution by which the balloon expansion speed is quickened by supplying fluid into the balloon through a through hole provided on the laser light absorbing heating tube. However, with the constitution noted in Patent Document 2 as well, the laser light absorbing heating tube has a metal braided structure, and in addition, a double structure part is provided on the laser light absorbing heating tube, so an increase in flexibility of the laser light absorbing heating tube was not yet realized.

Providing a gap in the braided structure of the laser light absorbing heating tube and increasing the flexibility of the laser light absorbing heating tube is also possible, but by doing that, when fluid is heated using laser light, there is the possibility of laser light leaking to outside the heating member. As a result, the heating efficiency by the laser light decreases, and there was the risk of a decrease in durability due to irradiation of laser light on the shaft or balloon.

BACKGROUND ART DOCUMENTS

Patent Documents

Patent Document 1: JP-B-2535250
Patent Document 2: JP-B-2864094

SUMMARY OF THE INVENTION

Problem the Invention Attempts to Solve

The present invention has been developed based on the circumstances described above as a background, and the problem it addresses is to provide a balloon catheter of a novel structure which is able to efficiently heat a heating element using laser light, which can ensure durability by preventing direct heating by laser light of the parts other than the heating element, and further to have excellent following capability in relation to the shape of the blood vessel.

Means for Solving the Problem

A first mode of the present invention provides a balloon catheter having a shaft and a balloon provided on a distal end section of the shaft, the balloon catheter being characterized by comprising: a tightly wound coil shaped heating element is housed and arranged in the balloon; an optical fiber that irradiates laser light being provided inside the heating element; a supply path for supplying a fluid that goes through an inside of the heating element to an inside of the balloon; and a discharge path that discharges the fluid from the inside of the balloon through a discharge port positioned outside the heating element.

With the balloon catheter constituted in accordance with this kind of first mode, by having the heating element be a tightly wound coil shape, it is possible to prevent leaking of laser light to the outer circumference side of the heating element, and to efficiently heat the heating element. In fact, it is possible to prevent direct irradiation by laser light of parts other than the heating element of the balloon and the like, which improves durability.

Furthermore, fluid such as normal saline solution or the like that fills the inside of the balloon is supplied through the interior of the heating element, and is also made to be discharged outside the heating element. Because of that, the fluid inside the balloon is stirred by flowing, and by the temperature distribution within the balloon becoming uniform, it is possible to prevent high temperatures or low temperatures in localized areas. In particular, by the heating element being provided at the inflow side of the fluid to the balloon, it is possible to more effectively make the temperature within the balloon constant.

Also, by being coil shaped, the heating element more easily bends and deforms. Because of that, deformation of the balloon catheter is allowed according to the shape of the blood vessel, and it is possible to prevent difficulty of insertion of the balloon to the blood vessel treatment site due to arrangement of the heating element, and it is also possible to avoid injury of the blood vessel due to unnecessary stress on the blood vessel wall.

Also, compared to a braided structure, the tightly wound coil shaped heating element is deformed easily by the pressure difference of the inner circumference side and the outer circumference side, and it is easy for a gap to arise between coils in the axial direction. Because of that, with a rise in fluid pressure at the inner circumference side of the heating element due to supplying of fluid, a sufficient volume of fluid flows from the inner circumference side of the heating element to the outer circumference side (balloon interior), and the balloon expands rapidly. Therefore, surgery time is shortened, and the burden on both the surgeon and the patient is reduced.

The second mode of the present invention is the balloon catheter in accordance with the first mode, wherein the heating element is arranged in a lengthwise direction of the shaft, and the laser light of the optical fiber is made to be irradiated from a side of a proximal end toward a side of a distal end of the heating element, and the distal end of the heating element is blocked.

With the second mode, laser light is made to be irradiated from the side of the proximal end of the heating element toward the side of the distal end, so laser light is irradiated evenly across the entire length of the heating element, and the entire heating element is heated. By doing this, the fluid is heated with excellent energy efficiency, making it possible to save energy.

Also, by the distal end of the heating element being blocked, it is possible to prevent laser light irradiated from the optical fiber from leaking to outside from the distal end of the heating element, and possible to realize efficient heating of the heating element, and also to more advantageously prevent a decrease in durability due to irradiation of laser light on the balloon or the like.

The third mode of the present invention is the balloon catheter in accordance with the second mode, wherein the heating element includes a part for which a coil inner diameter gradually becomes smaller in a taper shape across a designated length of the side of the distal end.

With the third mode, by the distal end part of the heating element being a tapered taper shape, the incidence angle of the laser light in relation to the inner surface of the distal end part of the heating element is adjusted, and it is possible to increase the projection opportunities and number of reflections of laser light on the inner surface of the heating element. As a result, the energy absorption efficiency of the heating element is increased, making it possible to more efficiently heat the heating element, and to reduce the laser energy.

Also, with the taper shaped part, the pressure due to inflow of fluid acts efficiently in the direction of releasing the contact between coils in the axial direction. Because of that, with the taper shaped part, it is relatively easy to cancel the coil abutment with the fluid inflow pressure, and it is easier for the fluid that has flowed in from the side of the proximal end to inside the heating element to flow out to the outside at the side of the distal end. By doing this, after the fluid has sufficient heat accumulation by moving inside the heating element from the side of the proximal end to the side of the distal end, it is flowed out to the outside of the heating element at the side of the distal end and while the heat of the heating element is transmitted to a tube such as the balloon and a blood vessel wall or the like, it moves to the side of the proximal end and flows out from the discharge port to outside the balloon. As a result, the entire balloon is warmed roughly uniformly, and it is possible to evenly warm the overall stenosis portion using the balloon.

The fourth mode of the present invention is the balloon catheter in accordance with any one of the first through third modes, wherein the supply path is formed by an inward side lumen that opens inside the balloon at the side of the distal end of the balloon, and the discharge path is formed by an outward side lumen that opens inside the balloon at the side of the proximal end of the balloon.

With the fourth mode, by having the supply path and the discharge path respectively formed by independent lumens, arranging the supply port at the side of the distal end and arranging the discharge port at the side of the proximal end within the balloon is easy.

The fifth mode of the present invention is the balloon catheter in accordance with any one of the first through fourth modes, wherein the heating element is inserted from a side of one axial direction in the inward side lumen that opens inside the balloon and supplies the fluid into the balloon, and the fluid flows in from an opening part of the one axial direction of the heating element.

With the fifth mode, by the heating element being inserted in the inward side lumen, the fluid sent to the balloon side through the inward side lumen flows into the inner circumference side of the heating element. By doing this, the fluid that has flowed into the balloon is heated rapidly by the heating element, and it is possible to prevent large fluctuations of the temperature inside the balloon due to new inflow of fluid, and it is also possible to prevent a decrease in temperature of the stenosis portion.

Effect of the Invention

With the present invention, by having the heating element be a tightly wound coil shape, when irradiating laser light from the inner circumference side of the heating element and heating the heating element, leaking of laser light to the outside is prevented, and it is possible to efficiently heat the heating element. In fact, the fluid supply path is provided at the inner circumference side of the heating element, and also, the fluid discharge path is provided outside the heating element, so stirring occurs within the balloon by the flowing of the fluid that reaches from the supply port to the discharge port, and it is possible to prevent extreme temperature differences from occurring within the balloon.

EMBODIMENTS FOR CARRYING OUT THE INVENTION

Figure 1:
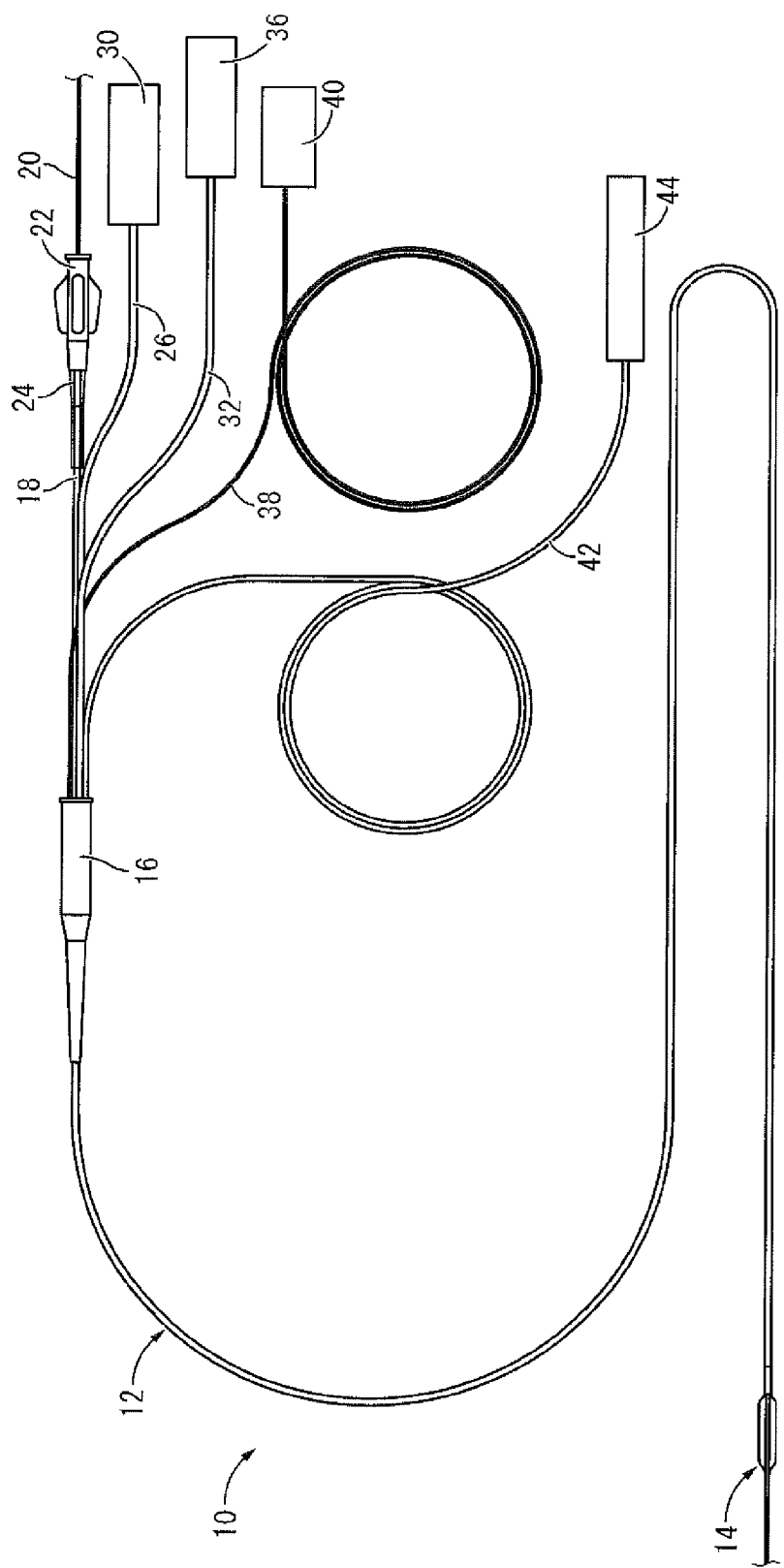
FIG. 1 is an explanatory view showing the balloon catheter as an embodiment of the present invention.

Following, we will describe embodiments of the present invention while referring to the drawings.

FIG. 1 shows a balloon catheter 10 as an embodiment of the present invention. The balloon catheter 10 is constituted including an external shaft 12 and a balloon 14 arranged at the side of the distal end of the external shaft 12.

In more detail, the external shaft 12 is a long shaped tube, and a port sleeve 16 is attached to the proximal end. The port sleeve 16 has a roughly taper shaped cylinder shape that gradually decreases in diameter toward the side of the distal end, and is formed with a relatively hard synthetic resin material or the like.

Also, an internal shaft 18 is inserted in the external shaft 12. The internal shaft 18 is a tube shaped member that can easily deform, and a guide wire 20 is inserted through a wire lumen (not illustrated) formed using the center cavity. Also, at the proximal end of the internal shaft 18, a hub 22 is attached. This hub 22 is a roughly cylinder shaped member formed using a hard synthetic resin material or the like the same as with the port sleeve 16, and is fixed to the proximal end of the internal shaft 18. A strain relief 24 is mounted on the connecting part of the internal shaft 18 and the hub 22, and bending of the internal shaft 18 at the attachment part to the hub 22 is prevented. Also, the shaft of this embodiment is constituted including the external shaft 12 and the internal shaft 18.

Also, an inward side tube 26 is inserted in the external shaft 12. The inward side tube 26 is a flexible tube, and a supply path is constituted by an inward side lumen 28 using its center cavity. Also, the inward side tube 26 is open at both lengthwise direction ends, and is formed so that a pair of through holes 29, 29 pierce through the radial direction in the circumference wall part of the side of the distal end. Also, an injection device 30 is mounted at the proximal end of the inward side tube 26, and by operating the injection device 30, fluid is flowed from the side of the proximal end of the inward side tube 26 through the inward side lumen 28 toward the side of the distal end, and the fluid inside the injection device 30 is sent out.

Also, an outward side tube 32 is inserted in the external shaft 12. The outward side tube 32 is the same kind of flexible tube as the inward side tube 26, and a discharge path is constituted by an outward side lumen 34 using its center cavity. Also, a suction device 36 is mounted on the proximal end of the outward side tube 32, and by operating the suction device 36, fluid flows from the side of the distal end of the outward side tube 32 through the outward side lumen 34 toward the side of the proximal end, and is sent into the suction device 36.

Also, a thermocouple 38 is inserted in the external shaft 12. As is generally known, the thermocouple 38 is an item for which wire rods formed of two different types of metal materials are connected to each other, and this is used as a thermoelectric thermometer that uses thermo-electromotive force. A plug 40 is provided at the proximal end of the thermocouple 38, and this is connected to a voltmeter or a potentiometer that are not illustrated. Then, by measuring the thermo-electromotive force using the voltmeter or potentiometer, and it is possible to measure the temperature of the normal saline solution filled inside the balloon 14 described later.

Also, an optical fiber 42 is inserted in the external shaft 12. The optical fiber 42 is a typical item formed with a dielectric spun using silica glass, plastic or the like as the material, and laser light is made to be transmitted from the proximal end of the optical fiber 42 to the distal end and irradiated from the distal end surface. A hub 44 is provided at the proximal end of the optical fiber 42, and is connected to a laser light irradiation device (not illustrated). Also, with the optical fiber 42, at least the distal end is inserted in an inward side lumen 28 described later.

The internal shaft 18, the inward side tube 26, the outward side tube 32, the thermocouple 38, and the optical fiber 42, respectively constituted as described above, are all inserted in the external shaft 12 from the opening part of the side of the proximal end of the port sleeve 16, and their distal ends project from the external shaft 12. Then, each projecting part from the external shaft 12 of the internal shaft 18, the inward side tube 26, the outward side tube 32, the thermocouple 38, and the optical fiber 42 is inserted in the balloon 14.

Figure 2:
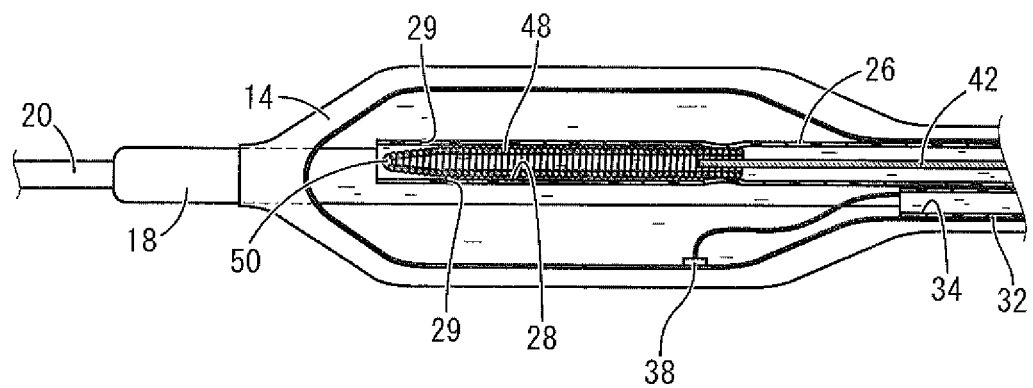
FIG. 2 is a cross sectional view showing an enlarged view of the key parts of the balloon catheter shown in FIG. 1.

As shown in FIG. 2, the balloon 14 is formed of a thin synthetic resin film or the like, and in an expanded state has a general bag shape as a whole. In more detail, both edge parts in the lengthwise direction have a tapered shape with a decreasing diameter toward the respective outsides, and the center part in the lengthwise direction is a round cylinder shape having a roughly constant diameter.

Then, the balloon 14 has its proximal end fixed by a means such as adhesion or the like to the distal end of the external shaft 12, and is arranged at the side of the distal end of the external shaft 12. Furthermore, the internal shaft 18 projecting from the external shaft 12 pierces in the lengthwise direction over the center axis of the balloon 14, and the distal end of the balloon 14 overlaps the distal end of the internal shaft 18 and is fixed by a means such as adhesion or the like. By doing this, the interior of the balloon 14 is separated from the exterior space in a fluid-tight manner, and by adjusting the internal pressure by sending in or discharging fluid such a normal saline solution or the like, it is possible to selectively switch between a contracted state during insertion or during extraction to the blood vessel stenosis portion, or an expanded state of expansion of the stenosis portion.

Also, each distal end of the inward side tube 26, the outward side tube 32, the thermocouple 38, and the optical fiber 42 projecting from the external shaft 12 is respectively arranged inside the balloon 14. Specifically, the distal end of the inward side tube 26 is arranged so as to be positioned at the distal end of the balloon 14, and the distal end of the outward side tube 32 is arranged so as to be positioned at the proximal end of the balloon 14. Furthermore, the distal end of the optical fiber 42 inserted in the inward side lumen 28 is arranged so as to be positioned at the proximal end of the balloon 14, and the distal end of the thermocouple 38 is fixed to the balloon 14.

Also, a coil member 48 is arranged in a housed state as the heating element at a site of the inward side tube 26 inserted inside the balloon 14. The coil member 48 is a linear hollow coil shaped member made by winding metal wire, and the coils are in a tightly coiled state overlapping indirectly and closely adhered in the axial direction. Also, the tightly wound coil shaped coil member 48 has elastic deformation occur by having the inner circumference side pressure be higher than the outer circumference side pressure, and a very small gap is formed between coils by that elastic deformation.

The metal wire (coils) constituting the coil member 48 can be rapidly switched between laser irradiation heating and cooling described later, so it is preferable to be fanned using a material with a low specific heat. Taking into consideration corrosion resistance and the like, the metal wire is made of nickel-chrome alloy, iron-chromium alloy or the like. Also, with the coil member 48 of this embodiment, the coils are continuously adhered along the entire circumference in a state without any acting of external force, but it is also possible to use a constitution for which the coils are partially adhered on the circumference, or a constitution having a very slight gap along the entire circumference, as a constitution with substantially sealed coils.

Also, with the coil member 48, at the part extending for a designated length of the side of the distal end, the coil inner diameter (the dimension correlating to the inner diameter of the coil at the coil member 48 which has a coil shape) gradually becomes smaller toward the side of the distal end, so that the part is tapered, and is separated from the inner circumference side in relation to the inward side tube 26. With this embodiment, the part that is a length of approximately ⅙ of the full length from the distal end of the coil member 48 is a tapered shape having a roughly fixed slope.

Furthermore, a cover member 50 is attached to the distal end of the coil member 48. This cover member 50 is a generally disk shaped or circular block shaped member formed with the same metal material as the coils, and the opening at the side of the distal end of the coil member 48 is blocked fluid-tight by the cover member 50. For example, by having an extremely small diameter for the distal end of the coil member 48, it is also possible to block the opening at the side of the distal end of the coil member 48 by the thickness of the coil itself.

Then, the coil member 48 is arranged along the lengthwise direction of the internal shaft 18, and is fit into the inward side lumen 28 along the entire length in the axial direction, and arranged concentrically on the inner circumference side of the inward side tube 26. By doing this, the fluid sent into the balloon 14 through the inward side lumen 28 flows into the inner circumference side from the opening of the side of the proximal end of the coil member 48, and is made to be supplied to inside the balloon 14 via the inner circumference area of the coil member 48. The outward side tube 32 is arranged at the outside of the coil member 48, and the opening (discharge port) to inside the balloon 14 of the outward side lumen 34 is arranged further to the side of the proximal end than the coil member 48.

Also, the optical fiber 42 inserted in the inward side lumen 28 of the inward side tube 26 has its distal end inserted into the proximal end of the coil member 48, and laser light is made to be irradiated at the inner circumference side of the coil member 48 from the side of the proximal end toward the side of the distal end.

The balloon catheter 10 constituted in this way is inserted into a blood vessel and the front end balloon 14 is aligned at the blood vessel stenosis portion. Alignment of the balloon 14 at the stenosis portion is realized by confirming the position of an imaging marker using a means such as X-ray illumination, for example. This imaging marker is formed using a metal material that is X-ray opaque, for example, and is a member having a ring shape or C shape, and arranged respectively at the proximal end and distal end of the balloon 14. When this kind of imaging marker is arranged, the thermocouple 38, the inward side tube 26 and the like can also be fixed in relation to the internal shaft 18 using the imaging marker.

Then, normal saline solution in which contrast medium is mixed (hereafter referred to as "normal saline solution") is sent from the side of the proximal end of the inward side lumen 28 into the balloon 14, and the normal saline solution within the balloon 14 is extracted from the side of the distal end of the outward side lumen 34. At that time, by making the volume of normal saline solution sent to the balloon 14 through the inward side lumen 28 greater than the volume of normal saline solution extracted from the balloon 14 through the outward side lumen 34, the internal pressure of the balloon 14 is raised, and the folded balloon 14 is made to expand. By doing this, the balloon 14 is pressed against the blood vessel wall, and the stenosis portion of the blood vessel has its diameter expanded by the pressing force of the balloon 14. The inflow of normal saline solution into the balloon 14 through the inward side lumen 28 and the extraction of the normal saline solution from within the balloon 14 through the outward side lumen 34 are realized by operating devices 30 and 36. Operation of the devices 30 and 36 can be performed manually or mechanically. Also, as described later, the normal saline solution, after being sent to the inner circumference side of the coil member 48, is made to be supplied to inside the balloon 14 through the gaps between coils.

In light of that, laser light is irradiated from the front end surface of the optical fiber 42 to the inner circumference surface of the coil member 48, and the coil member 48 is heated to a designated temperature by the laser light. Then, the heat of the coil member 48 is transmitted to the normal saline solution sent into the balloon 14 through the inward side lumen 28, and the normal saline solution is warmed. Furthermore, by the coil member 48 elastically deforming slightly by the fluid pressure of the normal saline solution that flows into its inner circumference side, normal saline solution leaks out from between coils in the axial direction to the outer circumference side of the coil member 48, and warmed normal saline solution is made to be supplied inside the balloon 14 through the opening of the side of the distal end of the inward side tube 26 and the pair of through holes 29, 29. By doing this, the heat of the normal saline solution is transmitted to the blood vessel wall of the stenosis portion via the balloon 14, and the flexibility of the blood vessel wall is increased at the stenosis portion. The reason for an increase in flexibility of the blood vessel wall may be due to softening of the elastic fibers (elastin) constituting the blood vessel wall due to the rise in temperature.

Simultaneous with this heating of the blood vessel wall, or delayed by a designated time, by expanding and deforming the balloon 14 and pushing open the blood vessel wall, it is possible to push open the more flexible blood vessel wall with low pressure. Because of that, injuries that occur to the blood vessel wall when pushing open using the balloon 14 are lessened, and it is possible to lighten the physical burden on the patient. The timing of expanding and deforming the balloon 14 is determined, for example, based on the balloon 14 temperature measuring results by the thermocouple 38.

Also, after heating and expansion of the blood vessel wall is performed using the balloon 14, with the expanded deformation state of the balloon 14 maintained, laser irradiation from the optical fiber 42 is stopped. Then, by newly inflowing normal saline solution into the balloon 14 through the inward side lumen 28, the temperature of the coil member 48 is reduced, and the blood vessel wall is rapidly cooled by the balloon 14. By doing this, the elastin constituting the blood vessel wall hardens, and the shape maintainability of the blood vessel wall in a state with the blood vessel stenosis portion expanded is increased. As a result, reconstricting of the blood vessel wall is inhibited even after the balloon 14 is contracted and extracted from the stenosis portion, and it is possible to sufficiently ensure blood flow. The normal saline solution that flows into the balloon 14 through the inward side lumen 28 is preferably adjusted to a temperature of approximately 40° C. according to the internal body temperature, but it is also possible to not perform a special temperature adjustment, and to send room temperature normal saline solution into the balloon 14.

With the balloon catheter 10 with this kind of constitution according to this embodiment, by pushing open the blood vessel wall while heating it using the balloon 14, the blood vessel wall is pushed open with low pressure, injury to the blood vessel wall is inhibited, and the physical burden on the patient is lightened. In fact, by inhibiting injury to the blood vessel wall, it is also possible to avoid restenosis of the blood vessel due to propagation of the intima at the time of injury treatment, so blood flow is ensured even after the procedure, and it is possible to continuously obtain a treatment effect.

Furthermore, the front end surface of the optical fiber 42 which is the laser light irradiating surface is inserted to the inner circumference side of the coil member 48, and the coil member 48 is efficiently heated by laser light across the entire circumference. In fact, by the coil member 48 being a tightly wound coil shape, it is possible to prevent leaking of the laser light to outside the coil member 48 through gaps between coils in the axial direction. Because of that, efficient heating of the coil member 48 is realized, and direct irradiation of laser light on other members of the balloon 14 or the like is prevented, thus preventing a reduction in durability.

Furthermore, by having the distal end of the coil member 48 be a tapered shape that gradually has the diameter decrease across a designated length toward the side of the distal end, the incidence angle of the laser light in relation to the inner circumference surface of the coil member 48 is adjusted. By doing this, the projection opportunities and number of reflections of the laser light on the coil member 48 increase, and the coil member 48 is heated efficiently, so it is possible to suppress laser light output and reduce the amount of power consumed.

In addition, the opening of the side of the distal end of the coil member 48 is blocked by the cover member 50. Because of that, laser light irradiated from the front end of the optical fiber 42 toward the side of the distal end is used effectively to heat the coil member 48, so it is possible to increase the heating efficiency of the coil member 48, and also to prevent leaking of laser light to the outside from the coil member 48, preventing a decrease in durability due to other members being heated.

Also, inside the balloon 14, between the opening part of the inward side tube 26 arranged at the side of the distal end and the opening part of the outward side tube 32 arranged at the side of the proximal end, flow of fluid occurs, so by stopping irradiation of the laser light, the temperature of the balloon 14 decreases rapidly. By doing this, rapid heating and cooling of the blood vessel wall is realized, and it is possible to effectively realize both the expansion of the stenosis portion with low pressure and holding of the expanded state at the stenosis portion after the balloon 14 is extracted.

Also, by having the heating element be a coil shaped coil member 48, curving and deformation is easier than with the heating element constituted in a tube shape with a mesh structure for the circumference wall part. Because of that, it is possible to prevent deformation of the balloon catheter 10 from becoming difficult at the coil member 48 arrangement site, and possible to easily insert the balloon 14 in the blood vessel stenosis portion. In fact, with the coil member 48, it is possible to have a tightly wound coil shape with the wires wound with no gaps while ensuring flexibility, and to avoid leaking of laser light to the outside.

Furthermore, by having the heating element be a coil shaped coil member 48, deformation is relatively easy by the pressure difference of the inner circumference side and the outer circumference side. Because of that, a sufficient volume of normal saline solution is supplied into the balloon 14 by the pressure of the normal saline solution sent to the inner circumference side of the coil member 48, and it is possible to rapidly expand the balloon 14. Therefore, the treatment time is shortened, and it is possible to lighten the physical burden and the mental burden of the surgeon and the patient.

While the present invention has been described in detail in its presently preferred embodiment, for illustrative purpose only, it is to be understood that the invention is by no means limited to the details of the illustrated embodiment, but may be otherwise embodied. For example, the coil member 48 does not absolutely have to be arranged in its entirety in a state housed inside the inward side lumen 28, and can also be partially just one end side in the axial direction inserted in the inward side lumen 28. More specifically, for example, the distal end of the coil member 48 including the cover member 50 can also be projecting from the distal end side opening of the inward side tube 26 to the distal end side, and be exposed inside the balloon 14.

Also, it is possible to use an external shaft of a constitution having a plurality of lumens, and use the lumens of the external shaft to form the supply path and discharge path of fluid for the balloon 14. Furthermore, it is also possible to have the guide wire lumen be constituted by the external shaft lumens, and in that case, it is possible to omit the internal shaft.

Also, by adhering the base end part of the inward side tube 26 to the outer circumference surface of the coil member 48, and tightly adhering it without gaps, it is also possible to have the entire volume of the normal saline solution supplied to the balloon 14 through the inward side lumen 28 sent to the inner circumference side of the coil member 48.

Keys To Symbols

10: Balloon catheter; 12: External shaft (shaft); 14: Balloon; 18: Internal shaft (shaft); 28: Inward side lumen (supply path); 34: Outward side lumen (discharge path); 42: Optical fiber; 48: Coil member (heating element)

The invention claimed is:
1. A balloon catheter comprising:
a shaft;
a balloon provided on a distal end section of the shaft;
a heating element located in the balloon and having a linear hollow coil shape including a metal wire wound in a closely-wound coiled state with the wound metal wire overlapped closely in an axial direction;
an optical fiber configured to irradiate a laser light, at least part of the optical fiber located inside the heating element;
a supply path configured to supply a fluid through an inside of the heating element to an inside of the balloon; and
a discharge path configured to discharge the fluid from the inside of the balloon through a discharge port positioned outside the heating element, wherein
the heating element is arranged in a lengthwise direction of the shaft,
the optical fiber is configured to irradiate the laser light from a side of a proximal end of the heating element toward a side of a distal end of the heating element,
the distal end of the heating element is blocked, and
the heating element includes a part for which a coil inner diameter gradually becomes smaller in a tape shape across a designated length of the side of the distal end.
2. The balloon catheter according to claim 1, further comprising:

an inward side lumen that forms the supply path, the inward side lumen being configured to open inside the balloon at a side of a distal end of the balloon, and an outward side lumen that forms the discharge path, the outward side lumen being configured to open inside the balloon at a side of a proximal end of the balloon.

3. The balloon catheter according to claim 1, wherein the heating element is configured to be inserted from a side of one axial direction in an inward side lumen, the inward side lumen being configured to open inside the balloon and supply the fluid into the balloon, and the fluid is configured to flow in from an opening part of the one axial direction of the heating element.

\* \* \* \* \*